(12) United States Patent
Ibrahim et al.

(10) Patent No.: US 10,018,592 B2
(45) Date of Patent: Jul. 10, 2018

(54) METHOD AND APPARATUS FOR SPATIAL COMPRESSION AND INCREASED MOBILITY RESOLUTION OF IONS

(71) Applicant: BATTELLE MEMORIAL INSTITUTE, Richland, WA (US)

(72) Inventors: Yehia M. Ibrahim, West Richland, WA (US); Sandilya Garimella, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/157,217

(22) Filed: May 17, 2016

(65) Prior Publication Data

US 2017/0336355 A1 Nov. 23, 2017

(51) Int. Cl.
*H01J 49/00* (2006.01)
*G01N 27/62* (2006.01)
*H01J 49/02* (2006.01)

(52) U.S. Cl.
CPC .......... *G01N 27/622* (2013.01); *H01J 49/022* (2013.01)

(58) Field of Classification Search
CPC ............................ G01N 27/622; H01J 49/022
USPC ........................................ 250/281, 282, 288
See application file for complete search history.

(56) References Cited

U.S. PATENT DOCUMENTS

| 5,572,035 A | 11/1996 | Franzen |
| 6,107,328 A | 8/2000 | Parsons |
| 6,960,760 B2 | 11/2005 | Bateman et al. |
| 7,365,317 B2 | 4/2008 | Whitehouse et al. |
| 7,391,021 B2 | 7/2008 | Stoermer et al. |
| 7,786,435 B2 | 8/2010 | Whitehouse et al. |
| 7,838,826 B1 | 11/2010 | Park |
| 7,888,635 B2 | 2/2011 | Belov et al. |
| 8,049,169 B2 | 11/2011 | Satake et al. |
| 8,222,597 B2 | 4/2012 | Kim et al. |
| 8,835,839 B1 | 9/2014 | Anderson et al. |
| 9,281,172 B2 | 3/2016 | Bateman et al. |
| 2004/0026611 A1 | 2/2004 | Bateman et al. |
| 2004/0031920 A1* | 2/2004 | Giles .................... G01N 27/622 250/287 |

(Continued)

FOREIGN PATENT DOCUMENTS

EP 1825495 B1 11/2011

OTHER PUBLICATIONS

Nieminen, A., et al., Beam cooler for low-energy radioactive ions, Nuclear Instruments and Methods in Physics Research A, 469, 2001, 244-253.

(Continued)

*Primary Examiner* — Nicole Ippolito
*Assistant Examiner* — Hanway Chang
(74) *Attorney, Agent, or Firm* — Klarquist Sparkman, LLP (57) ABSTRACT

Methods and apparatuses for ion peak compression and increasing resolution of ions are disclosed. Packets of ions are introduced into a device. A first electric field is applied for dispersing the ion packets temporally or spatially according to their mobilities. A second intermittent traveling wave is applied for regrouping or merging the dispersed ion packets into a lesser number of trapping regions with narrower peaks. The ions packets are compressed into the narrower peak regions by varying a duty cycle of the intermittent traveling wave.

31 Claims, 10 Drawing Sheets

(56) References Cited

U.S. PATENT DOCUMENTS

2007/0138384 A1    6/2007   Keiser
2011/0049357 A1    3/2011   Giles
2011/0192969 A1    8/2011   Verentchikov

OTHER PUBLICATIONS

Pervukhin, V. V., et al., Ion Peak Narrowing by Applying Additional AC Voltage (Ripple Voltage) to FAIMS Extractor Electrode, J Am Soc Mass Spectrom, 21, 2010, 47-52.

* cited by examiner

METHOD AND APPARATUS FOR SPATIAL COMPRESSION AND INCREASED MOBILITY RESOLUTION OF IONS

STATEMENT REGARDING FEDERALLY SPONSORED RESEARCH OR DEVELOPMENT

This invention was made with Government support under Contract DE-ACO576RLO1830 awarded by the U.S. Department of Energy. The Government has certain rights in the invention.

TECHNICAL FIELD

This invention relates to ion spatial compression, accumulation, and increasing mobility resolution of ion separations. More specifically, this invention relates to compressing distributions of ions into narrower peaks or redistribution of ion peaks by applying an intermittent traveling wave, resulting in increased signal-to-noise ratio and peak resolution.

BACKGROUND

In a traveling wave (TW) separation, ions of different mobilities separate based on their relative motion in a moving electric field, typically by the intermittent application of DC voltages. This TW profile moves in the intended direction of ion motion. The TW creates periodic highs and valleys, and the ions are trapped in valleys if the field moves very slowly relative to their mobilities. As the TW moves forward, depending on the speed of motion of the TW, the ions either stay within their valley or roll over the wave to fall back into the previous potential valley. The number of such rollovers is dependent on the ion mobility of the species and this leads to mobility based separation; species with lower mobilities roll over more often and take longer periods to traverse a given distance.

With conventional ion mobility separations, larger voltages are required as the separation distance is increased, as in traditional mobility separations that use constant drift fields. Thus, extremely long path length separations are not feasible. TW based separations can be used to avoid this limitation, however limitations still persist. The practical realization of the benefit of TW ion mobility separations is limited by considerations that include the peak broadening due to diffusion ion roll over in the traveling waves. This results in broad peaks for ion mobility separations when using very long path lengths, making detection difficult and signal-to-noise (S/N) low. Further, multi-pass/cyclical path ion mobility separations are similarly limited in their extent due to peak broadening and signal dilution at large number of passes. Indeed, for such devices one peak can expand by such effects to fill the entire path, and making the approach ineffective for even species of very similar mobility. The solution to this problem for TW separations would enable overcoming diffusional/peak broadening related issues and allow novel instrumentation providing very high ion mobility spectrometry (IMS) resolution.

A related challenge in such application is to increase the initial ion population significantly, so as to increase the S/N at the time of detection, but space charge effects limit the size of the ion population that can initially injected for IMS separations. Thus, while an ion trap is often used to accumulate ions for injection to IMS, a key limitation is the space charge capacity that limits the maximum number of charges, typically to about $10^6$ or at most $10^7$. While the initial injection pulse can be made greater by extending it over a longer period, a longer injection pulse also makes peaks wider and is incompatible with the desired higher resolution. No solution to the problem has been evident, resulting in the need to often repeat the separation many times, and then sum or average the results, to improve the S/N.

In IMS, achieving high resolution has been traditionally addressed by: 1) increasing the physical size of the IMS cell by building a long path length, 2) increasing the pressure, and 3) in a few cases, circulating ion packets in cyclic or multi-pass devices. Increasing the physical size of the IMS cell is hindered by the practicality of fabricating such systems and, in the case of constant field IMS, increasing the physical length requires a proportional increase of the drift voltage. The maximum drift voltage is limited by the electrical breakdown phenomena. Alternatively, the pressure of the buffer gas can be increased which is, however, accompanied by a significant loss of ions due to the poor ability to trap ions at high pressure over extended periods. Increasing the pressure also requires a proportional increase of the drift voltage in constant field IMS which, as mentioned above, is limited by the breakdown voltage. Finally, the path length can be increased by circulating ion packets multiple times in a cyclotron device in order to achieve high resolution. However, the number of passes that can be usefully applied is progressively limited by both the increasing separation between ions and the increased size of the peak, and ultimately as one peak fills the entire device. The length of the cyclic or multi-pass arrangement can be made greater to increase the range of mobilities that can be separated simultaneously, however such devices are cumbersome and difficult to fabricate. As such, there is a need for novel approaches to solve the aforementioned challenges.

SUMMARY

The present invention is directed to methods and apparatuses for ion spatial compression and increasing resolution of ions in IMS, or increasing the S/N following other separations. In one embodiment of the present invention, an apparatus for peak ion compression is disclosed. The apparatus includes a device into which a substantially continuous beam of ions is introduced. The apparatus also includes an intermittent traveling wave applied to the device for compressing the ions into a narrower distribution of ion peaks. In one embodiment, the ion packets are compressed into the narrower distribution of peaks by varying a duty cycle of the intermittent traveling wave.

In one embodiment, the reduction in peak distribution widths occurs due to a substantial continuous incoming beam being merged into a single trap at the interface between a normal (non-intermittent) traveling wave and the intermittent traveling wave portions of the device.

In another embodiment, the present invention is used in multi-pass designs to trap and accumulate much larger ion populations and then spatial compression applied at different times during the separation, resulting in greatly increased S/N in conjunction with much greater IMS resolution.

In another embodiment of the present invention, a method of ion peak compression is disclosed. The method includes introducing a substantially continuous beam of ions into a device. The method also includes applying an intermittent traveling wave to the device for compressing the ions into narrower ion peaks.

In another embodiment of the present invention, an apparatus for ion peak compression is disclosed. The apparatus includes a device into which packets of ions are introduced.

The apparatus further includes a first electric field for dispersing the ion packets temporally or spatially according to their mobilities. The apparatus also includes a second intermittent traveling wave for regrouping or merging the dispersed ion packets into a lesser number of trapping regions with narrower peaks. In one embodiment, the ion packets are merged into the narrower peak regions by varying a duty cycle of the intermittent traveling wave.

The first electric field may be a continuous traveling wave field formed according to the description provided in U.S. Patent Application 62/238,291 filed 7 Oct. 2015 entitled Method and Apparatus for Controlling Ions in a Gas Phase, the entirety of which is hereby incorporated by reference.

In one embodiment, the first electric field is applied to a first region of ion motion and the second intermittent traveling wave (or "stuttering" wave) is applied to a second region of ion motion. The direction of ion motion in the first electric field region can be orthogonally aligned or aligned in the same direction to the direction of ion motion in the second intermittent traveling wave region. Alternatively, the first electric field region and the second intermittent traveling wave region may be aligned at any angle between 0°-359° relative to one another.

In one embodiment, the intermittent traveling wave merges ions from two or more trapping regions into one. In another embodiment, the intermittent traveling wave merges ions from four or more trapping regions into one.

In one embodiment, the intermittent traveling wave may be replaced with a non-intermittent traveling wave after a predetermined range of ion packets are regrouped or merged into the narrower peak regions and prior to detection.

In another embodiment of the present invention, a method of ion peak compression is disclosed. The method includes introducing packets of ions into a device. The method further includes applying a first electric field for dispersing ion packets into multiple trapping regions. The method also includes applying a second intermittent traveling wave for regrouping or merging the dispersed ion packets into a lesser number of trapping regions with narrower peaks.

In another embodiment of the present invention, a method of increasing resolution of ions in IMS is disclosed. The method includes introducing packets of mixed ions into an IMS device. The method further includes separating the ions according to their mobilities by applying a constant or variable electric field to the device. The method also includes reversing the electric field to move the ion packets to a position prior to the separating step; and repeating the separating and reversing steps until a desired resolution is attained. The method effectively increases a path length for IMS separations without physically increasing the IMS device.

The electric field of the reversing step is different from the electric field of the separating step.

In one embodiment, the method further comprises, after the step of separating the ions and/or the step of reversing the electric field, compressing the ion packets.

In one embodiment, no ion separation occurs during the reversing step.

The reversing step may include decreasing the speed or increasing the amplitude of the electric field.

In another embodiment of the present invention, an apparatus for increasing resolution of ions in IMS is disclosed. The apparatus includes an IMS device in which packets of mixed ions are introduced. The apparatus further includes a constant or variable electric field applied to the device for separating the ions according to their mobilities. The apparatus also includes an ion compressor for narrowing or compressing the ion peaks; and the application of TWs in the opposite direction under conditions where no separation occurs, e.g. using a higher TW amplitude, to move the ion packets to a position prior to when the constant or variable electric field or TW is applied for the ions separations.

In another embodiment of the present invention, an apparatus for increasing resolution of ions from any separation prior to ionization is disclosed. This includes ions formed after e.g. GC or LC separations, and applying TW peak compression to benefit the S/N during detection.

In one embodiment, a liquid phase separation is followed by conversion to gas phase ions that are then injected into the region where the intermittent/stuttering traveling wave is applied for peak compression.

In another embodiment of the present invention, an apparatus used in conjunction with long path length and/or multi-pass traveling wave IMS devices, such as the device described in U.S. Pat. No. 8,835,839, hereinafter referred to as Structures for Lossless Ion Manipulations (SLIM) devices, is disclosed.

In another embodiment of the present invention, an apparatus for increasing resolution of ions in IMS is disclosed. The apparatus includes an IMS device in which a large packet of ions or a continuous beam of ions is introduced. The apparatus further includes an ion compressor for partially narrowing or compressing the volume in which the ions are trapped. The apparatus also includes a TW, constant or variable electric field applied to the device for partially separating the ions according to their mobilities. The apparatus also includes the additional use of the compressor for narrowing or compressing the ions and that is applied after space charge effects are reduced due to the partial separation, so as to produce a final separation with much greater peak intensities and S/N.

In another embodiment of the present invention, an apparatus for increasing resolution of ions after any separation device such as, but not limited to, a GC or LC is disclosed. The apparatus includes a device in which packets of ions from a separation are introduced. The apparatus also includes an ion compressor applied prior to detection for narrowing or compressing the ions in the peaks from the separation.

In another embodiment of the present invention, an apparatus for increasing resolution and S/N detection of ions in SLIM IMS is disclosed. The apparatus includes a SLIM IMS device in which a large packet of ions or continuous beam of ions is introduced for a period. The apparatus also includes an initial ion compressor applied for partially narrowing or compressing the ions. The apparatus also includes a constant or variable electric field applied to the device for partially separating the ions according to their mobilities. The apparatus further includes an additional ion compressor for narrowing or compressing the ions, applied after space charge effects are reduced due to the partial separation, so as to produce a final separation with much greater peak intensities and S/N.

In another embodiment of the present invention, an apparatus for increasing resolution and S/N detection of ions from a separation in SLIM IMS is disclosed. The apparatus includes a SLIM device in which a large packet of ions are introduced or a continuous beam of ions is introduced for some period. The apparatus also includes an initial ion compressor applied for partially narrowing or compressing the ions. The apparatus also includes a constant or variable electric field applied to the device for partially separating the ions according to their mobilities. The apparatus further includes an additional ion compressor for narrowing or compressing the ions, applied after space charge effects are reduced due to the partial separation, so as to produce a final separation with much greater peak intensities and S/N.

BRIEF DESCRIPTION OF THE DRAWINGS

FIGS. 2A-2C shows the results of spatial peak compression using the apparatus of FIG. 1. FIG. 2A is the initial distribution of the ion peak spread, and FIGS. 2B and 2C involving application of the intermittent traveling wave having a narrowing effect on the distribution of the ions.

DETAILED DESCRIPTION OF THE PREFERRED EMBODIMENTS

The following description includes preferred embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Disclosed are methods, devices, and apparatuses for increasing signal-to-noise ratio in traveling wave ion mobility and other applications in which ions are separated based on their mobilities when an external force, e.g., a voltage field, is imposed on the ions, or separated by other means, including before ionization. The present invention includes the imposition of an intermittent or "stuttering" traveling wave that sorts, compresses, or regroups ions into fewer mobility 'bins', where bin is defined herein as one of the trapping regions between two waves. Signal intensity increases as a result of this binning of ions with the same or very similar mobilities. Any loss of resolution as a result of peak bunching can be regained by a short additional drift time after the sorting/regrouping/compressing step. This "rebinning" can simply be combining each two or more adjacent bins into one—i.e. giving a compression ratio of 2 or larger integer value, but other more complex rebinnings are feasible, and where the compression ratio varies or is programmed in a certain fashion, to e.g. apply greater compression as peaks get broader during a separation.

The present invention also discloses methods, devices, and apparatuses for increasing the resolution of traveling wave ion mobility separations by effectively increasing the path length for achieving IMS separations without physically increasing the IMS device or cell. Thus, the same path length may be utilized multiple times as desired to achieve high resolution.

Figure 1:
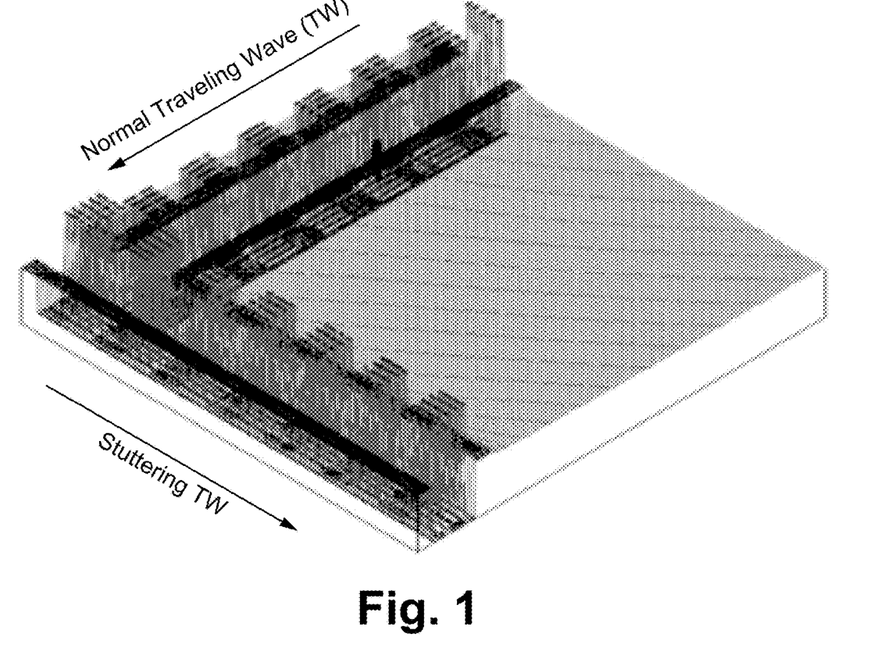
FIG. 1 is a schematic diagram of an apparatus for ion peak compression including a normal traveling wave and a "stuttering" or intermittent traveling wave, in accordance with one embodiment of the present invention. Linear and other arrangements are also practical.

FIG. 1 is a schematic diagram of an apparatus for ion mobility separations, in accordance with one embodiment of the present invention. As ions are introduced into the apparatus or device, a traveling wave electric field is applied for separating the ion packets temporally or spatially according to their mobilities. As such, the ions are dispersed or spread out over multiple traveling traps or bins. When this "normal" or continuously moving traveling wave is interfaced with a second region where a "stuttering" or intermittent traveling wave—where the moving traveling wave stops intermittently—the ions which are spread out over the multiple trapping bins of the normal traveling wave get repopulated into a lesser number of trapping regions with narrower peaks. Thus, the ions that were dispersed over a long path of many traveling traps are sorted into a different, narrower distribution involving a smaller number of bins.

The extent of such repopulation is dependent on the duty cycle of the intermittent traveling wave, i.e. the relative time for which the traveling wave stops and moves. After a chosen or predetermined range of ion mobility peaks are so re-populated, the intermittent traveling wave can be replaced with a normal traveling wave. This can occur prior to detection A higher signal-to-noise ratio is achieved as a result of the regrouping of ions with similar mobilities into narrower mobility bins or traps. By interfacing the two electric fields—the normal traveling wave and the intermittent traveling wave—repeatedly, say, in a multiple pass type of separation, a larger number of cycles will be enabled. By appropriately choosing the frequency and order of such peak bunching, practically infinite peak resolution may be feasible.

Figure 2A:
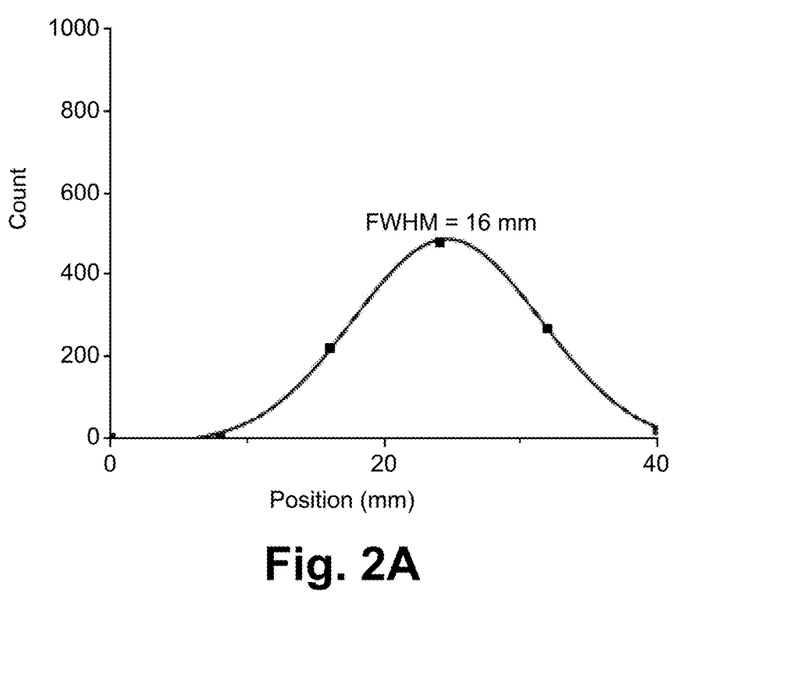
Figure 2B:
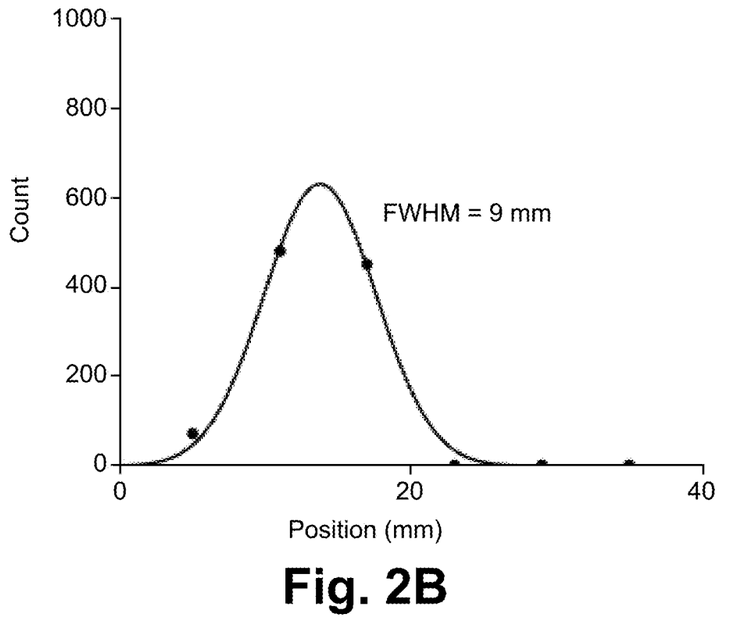
Figure 2C:
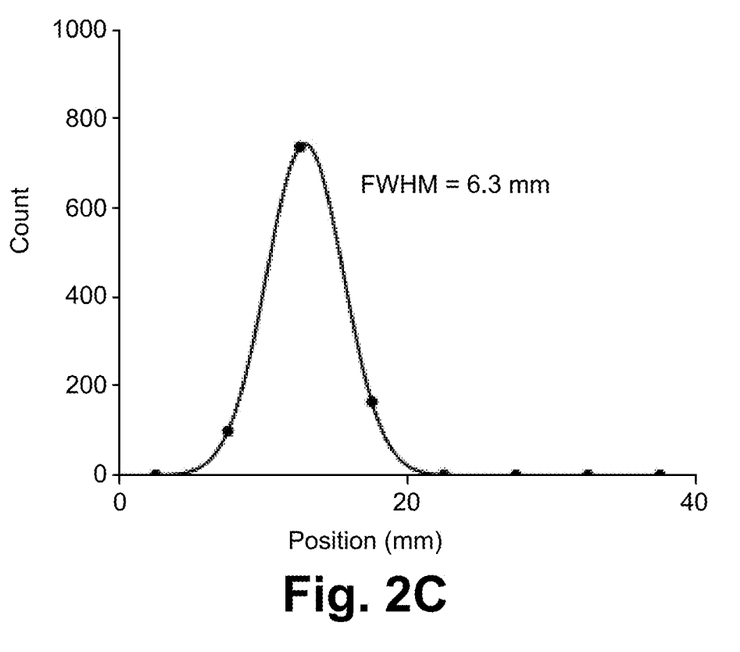

FIGS. 2A-2C shows the results of spatial peak compression using the apparatus of FIG. 1. FIG. 2A is the initial distribution or peak of the ions spread over 48 electrodes in this example. The full width half maximum (FWHM) for the initial distribution was approximately 16 mm.

FIGS. 2B and 2C show the narrowing effect on the distribution of the ions when the intermittent traveling wave is applied. In FIG. 2B, ions in two bins are merged into one, and the FWHM is reduced to approximately 9 mm. FIG. 2C shows the effect of merging 4 bins of ions into one. The FWHM in FIG. 2C is decreased further to approximately 6.3 mm, leading to an increase in signal-to-noise ratio.

Figure 3A:
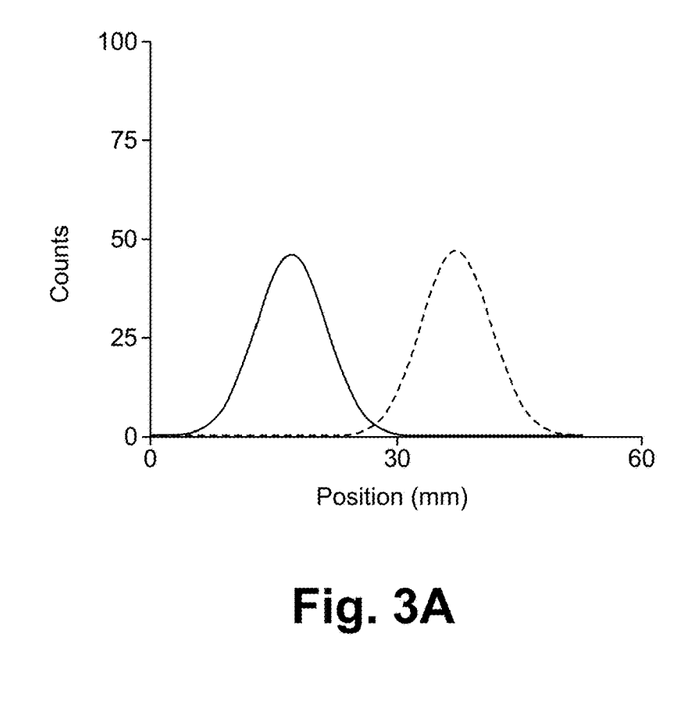
FIGS. 3A and 3B shows the spatial peak compression with no compression (FIG. 3A) and with 2× compression after imposition of the intermittent traveling wave (FIG. 3B).
Figure 3B:
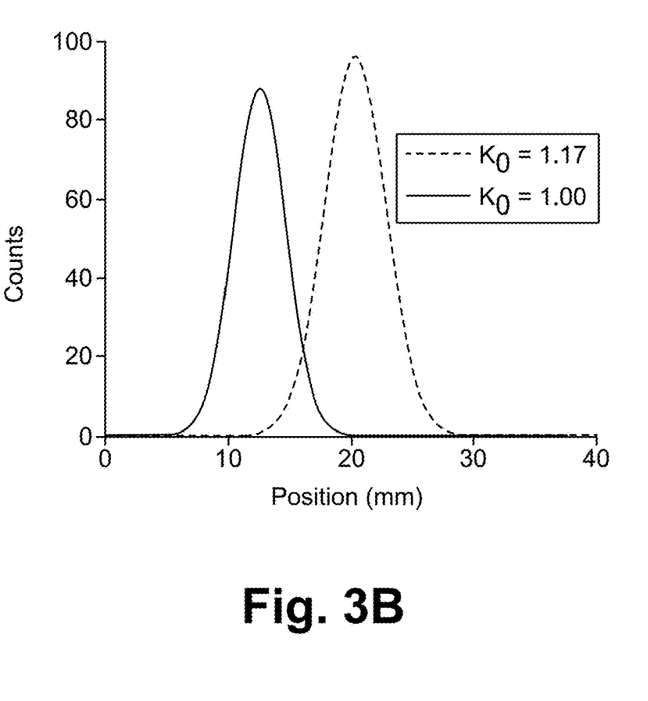

FIGS. 3A and 3B shows the spatial peak compression with no compression (FIG. 3A) and with 2× compression after imposition of the intermittent traveling wave (FIG. 3B), for two ions with different mobilities—$K_0$=1.17 cm$^2$/V·s and $K_0$=1.00 cm$^2$/V·s.

Figure 4A:
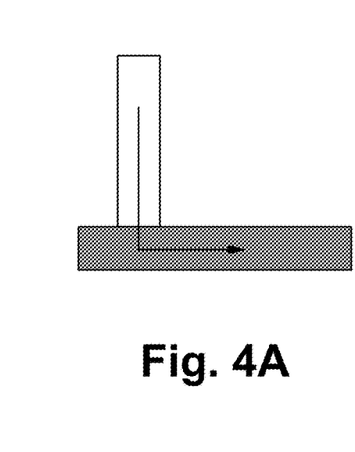
FIG. 4A shows ion motion through a separation region orthogonally aligned to a compressor region of the apparatus, in accordance with one embodiment of the present invention.
Figure 4B:
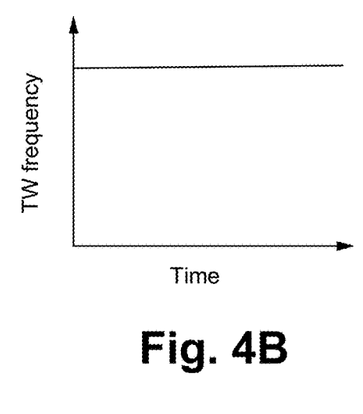
FIG. 4B is a graph of frequency over time for a normal traveling wave applied to the separation region.
Figure 4C:
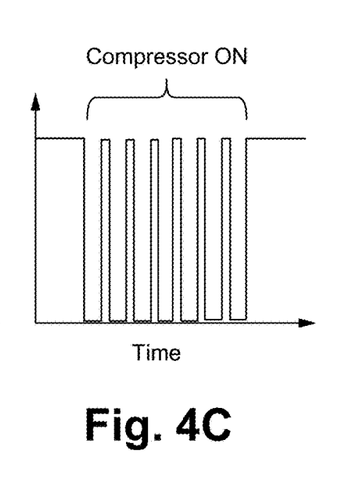
FIG. 4C is a graph of frequency over time for the intermittent traveling wave applied to the compressor region of the apparatus.
Figure 5:
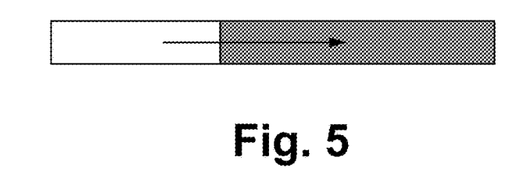
FIG. 5 is one variation of the separation and compressor regions, with the two regions aligned in the same or similar direction.

FIG. 4A shows ion motion through a separation region orthogonally aligned to a compressor region of the apparatus, in accordance with one embodiment of the present invention. The normal traveling wave region, referred to as the separation region, has a constant traveling wave frequency as shown in the graph of FIG. 4B and is, in this example, vertically oriented and orthogonal to the intermittent traveling wave region. The intermittent traveling wave region, referred to as the compressor region, has an intermittently non-zero traveling wave frequency as shown in the graph of FIG. 4C and is, in this example, horizontally oriented. The arrow indicates the ion trajectory path FIG. 5 is one variation of the separation and compressor regions of FIG. 4A, with the two regions aligned in the same or similar direction. The effect on signal-to-noise and resolution when the regions are aligned in the same direction is similar to the orthogonal orientation of FIG. 4A.

Figure 6:
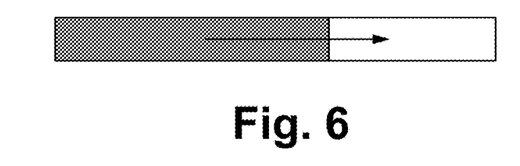
FIG. 6 is another variation of the separation and compressor regions, with the compressor region preceding the separation region.

FIG. 6 is another variation of the separation and compressor regions of FIG. 4A and FIG. 5, with the compressor region preceding the separation region. The configuration of FIG. 6 may be useful, for example, when ion trapping or separating prior to ion compression is not necessary; the compressor is used as an injection device for subsequent separation.

Figure 7:
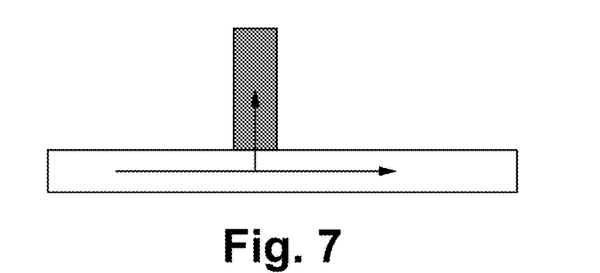
FIG. 7 is another variation of the separation and compressor regions, which includes dynamically gating ions into either of the two regions.

FIG. 7 is another variation of the separation and compressor regions for devices that include dynamically gating ions into either of the two regions, namely the separation and compressor regions.

Figure 8A:
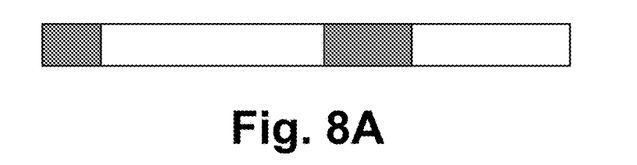
FIGS. 8A, 8B, and 8C are variations of the separation and compressor regions, with any combination of relative size and relative position of the two regions.
Figure 8B:
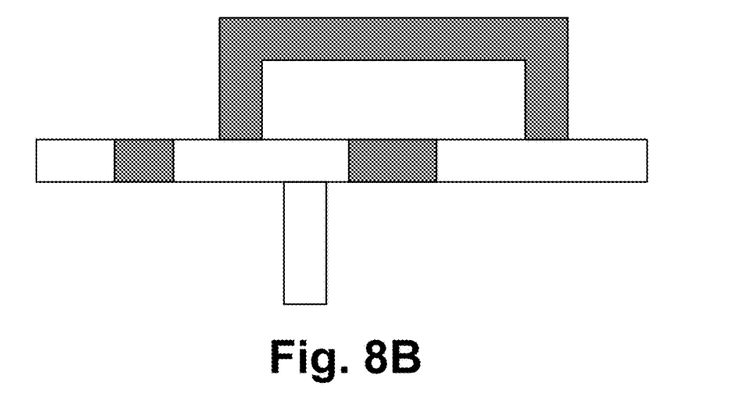
Figure 8C:
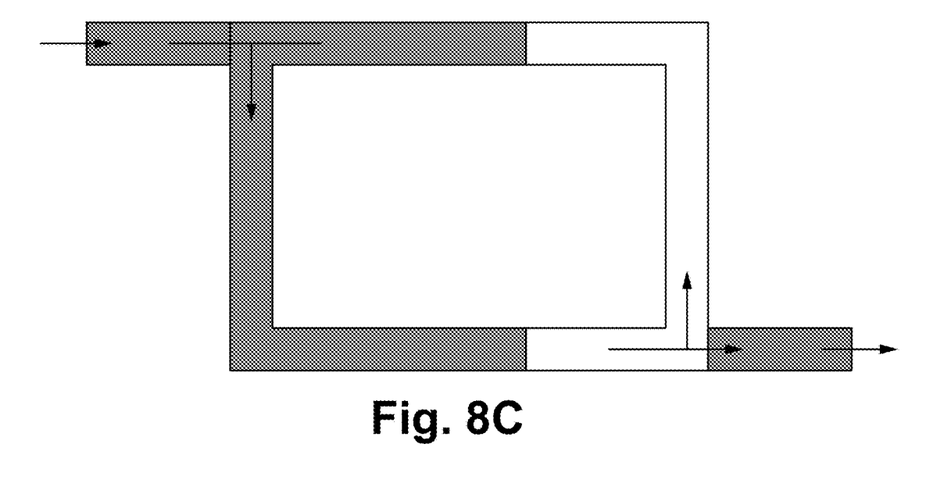

FIGS. 8A, 8B, and 8C are variations of the separation and compressor regions, with any combination of relative size and relative position of the two regions. FIG. 8A shows a compressor region followed by a separation region, and then a repeat of the same pattern. FIGS. 8B and 8C show the regions configured with or in orbital motion.

Figure 9A:
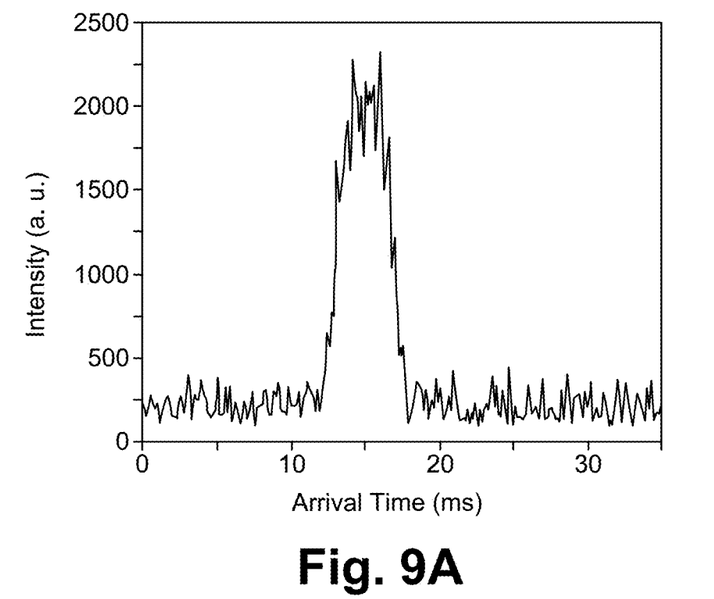
FIGS. 9A and 9B show the arrival time distribution and intensities of a non-compressed ion packet (FIG. 9A) and a compressed ion packet (FIG. 9B).
Figure 9B:
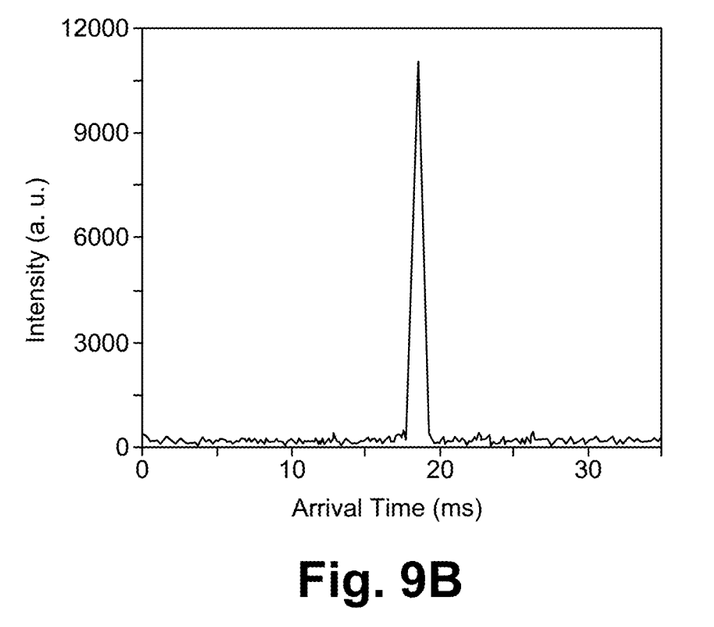

FIGS. 9A and 9B show the arrival time distribution and intensities of a non-compressed ion packet (FIG. 9A) and a compressed ion packet (FIG. 9B).

Figure 10A:
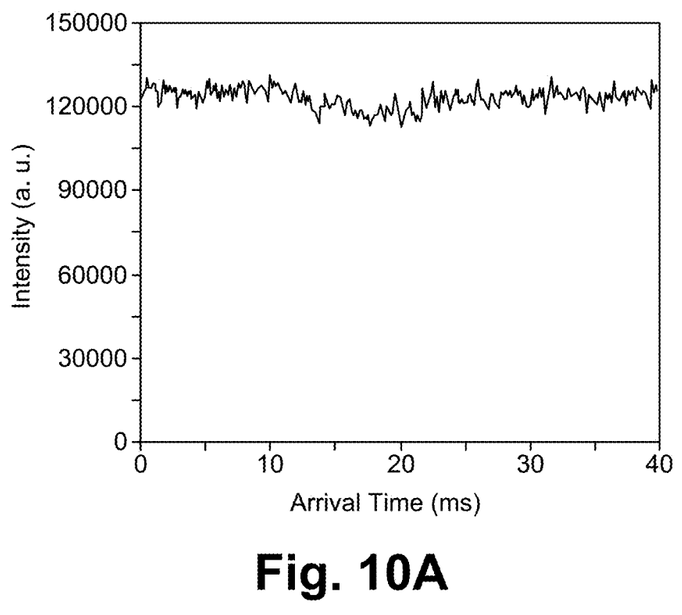
FIGS. 10A and 10B show the arrival time distribution and intensities of a non-compressed continuous ion beam (FIG. 10A) and a compressed continuous ion beam (FIG. 10B).
Figure 10B:
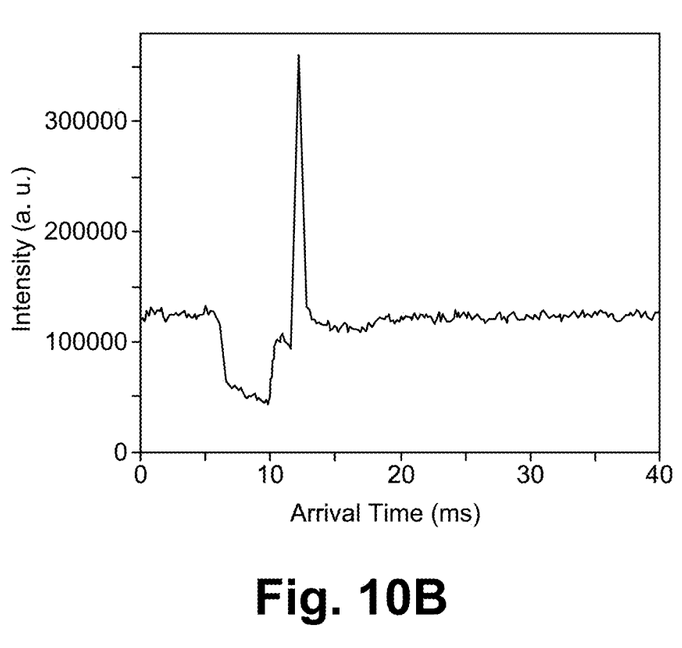

FIGS. 10A and 10B show the arrival time distribution and intensities of a non-compressed continuous mode ion beam (FIG. 10A) and a compressed continuous mode ion beam (FIG. 10B).

Figure 11:
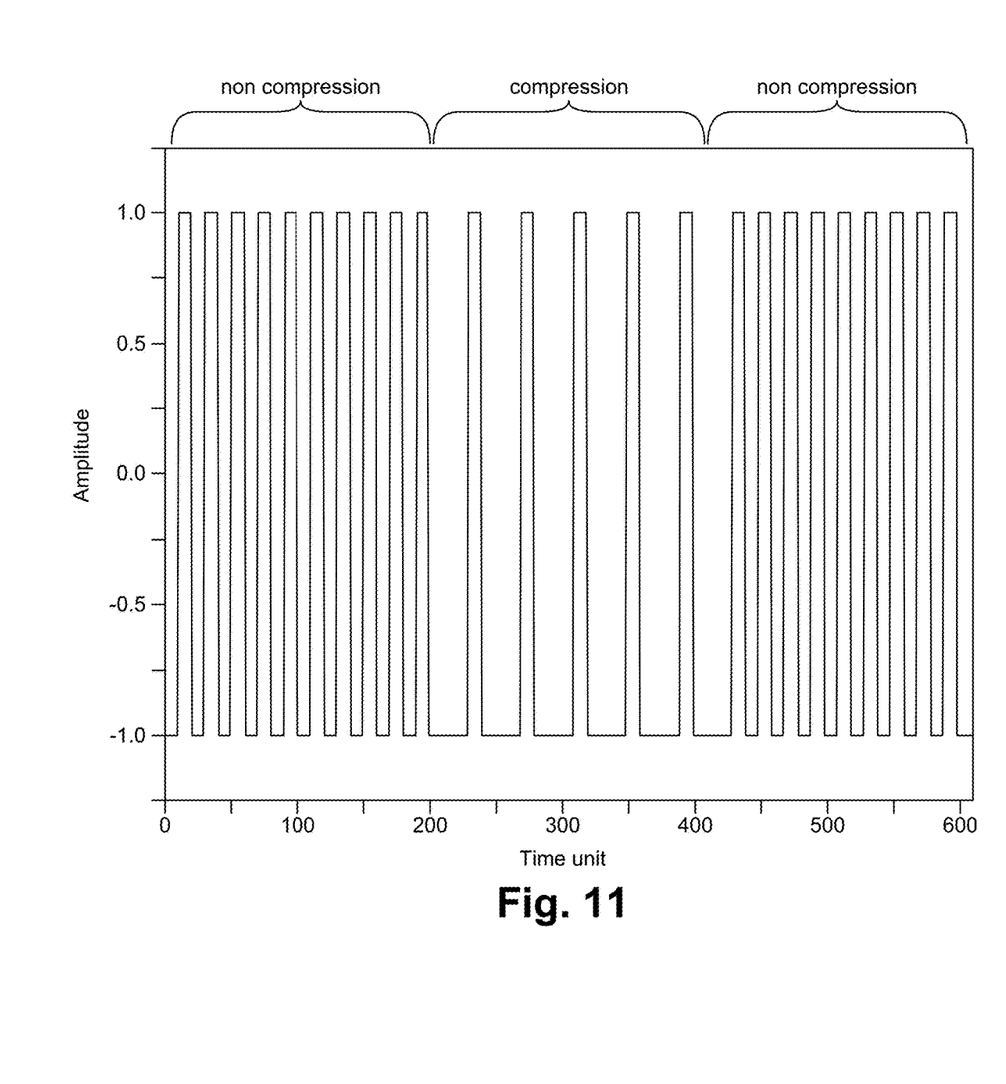
FIG. 11 illustrates change in duty cycle when the voltage is applied to one of the compressor electrodes of FIG. 1 over time. Initially there is no compression, then the duty cycle changes to allow the compression, and then after a certain time the duty cycle is changed to a different duty cycle which may be similar or different to the initial duty cycle.

FIG. 11 illustrates change in duty cycle when the voltage is applied to one of the compressor electrodes of FIG. 1 over time. Initially there is no compression, then the duty cycle changes to allow the compression, and then after a certain time the duty cycle is changed to a different duty cycle which may be similar or different to the initial duty cycle.

Figures 12, 13A:
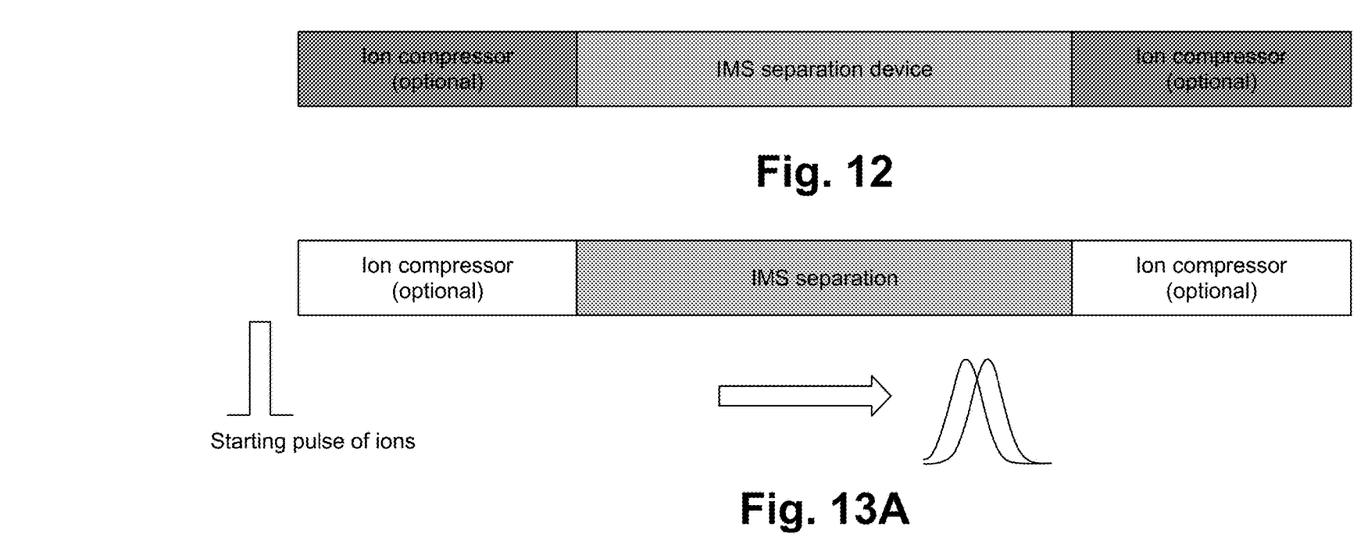
FIG. 12 is a simplified block diagram of an apparatus for increasing resolution in IMS, in accordance with one embodiment of the present invention.
FIGS. 13A-13E show the different stages, some optional, for increasing resolution in IMS, in accordance with one embodiment of the present invention, including ion separation (FIG. 13A), optional ion compression with reversing of the electric field direction (FIG. 13B), ions moving back to a position prior to the separation stage (FIG. 13C), optional ion compression (FIG. 13D), and repeating, if considered necessary, ion separation until a desired resolution is obtained (FIG. 13E).

FIG. 12 is a simplified block diagram of an apparatus for increasing resolution in IMS, in accordance with one embodiment of the present invention. The apparatus includes an optional ion compressor coupled to an IMS separation device which is further coupled to another optional ion compressor.

Figure 13B:
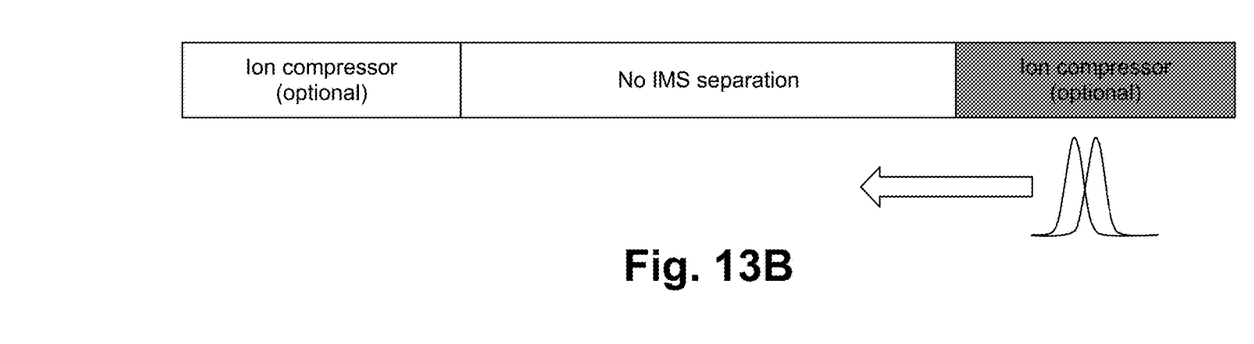
Figures 13C, 13D:
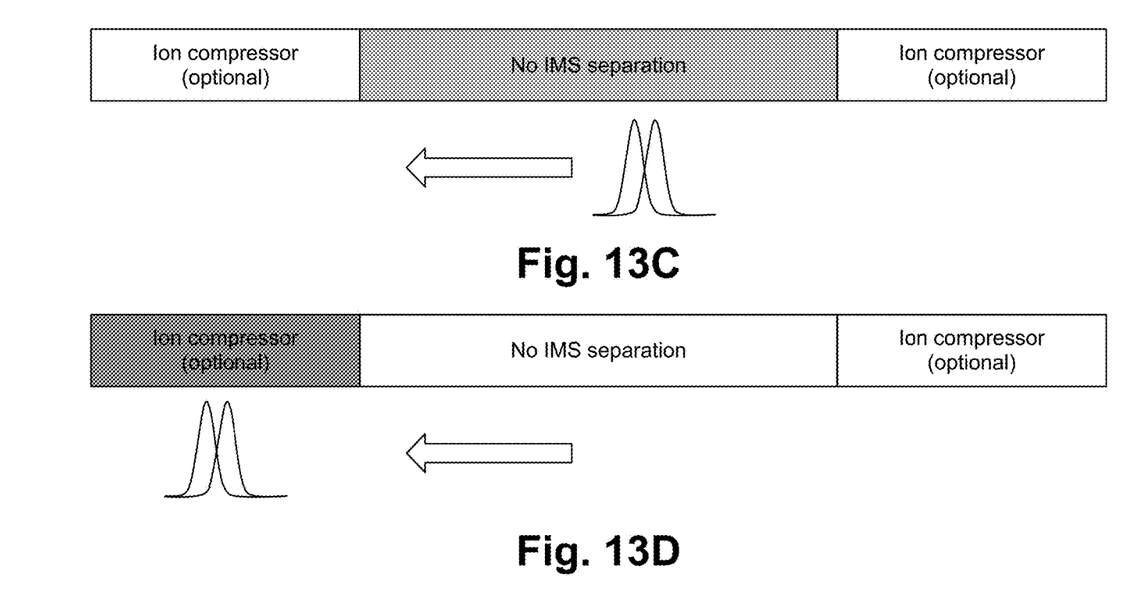
Figure 13E:
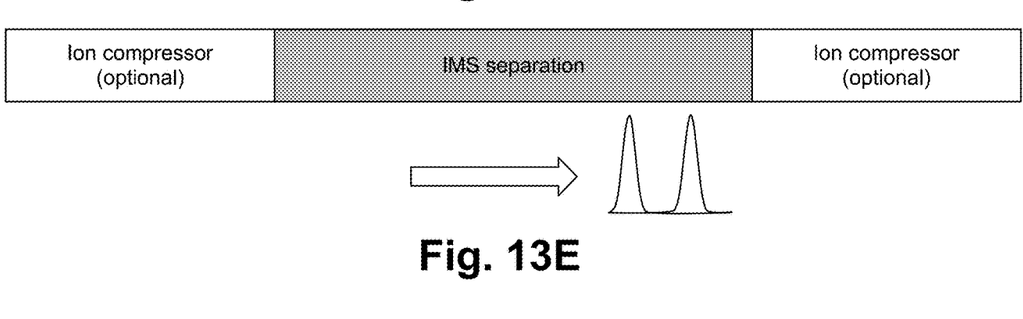

FIGS. 13A-13E show the different stages, some optional, for increasing resolution in IMS, in accordance with one embodiment of the present invention. In FIG. 13A, pulsed ions are introduced into an IMS device where they are then separated according to their mobilities by applying a constant or variable electric field to the device. Next, in FIG. 13B, an optional ion compressor narrows or compresses the ions, and the electric field is reversed. Reversing the electric field causes the ions to move back to a position prior to the separation stage, as shown in FIG. 13C. Another optional ion compression stage is shown in FIG. 13D. No IMS separation occurs between FIGS. 13B-13D. The process may be repeated, as shown in FIG. 13E, until a desired resolution is obtained.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. An apparatus for ion manipulation comprising:
a first region configured to receive ions and generate a first electric field, the first electric field comprising a travelling wave configured to disperse the ions into a plurality of ion packets based on mobility of the ions; and
a second region separate from the first region and configured to receive the plurality of ion packets and generate a second electric field forming an intermittent traveling wave having a duty cycle, the intermittent traveling wave configured to merge two or more adjacent ion packets of the plurality of ion packets by varying the duty cycle.

2. The apparatus of claim 1, wherein the ion packets are regrouped or merged into narrower peak regions by variation of the duty cycle of the intermittent traveling wave.

3. The apparatus of claim 1, wherein the first electric field is a traveling wave.

4. The apparatus of claim 1, wherein the direction of ion motion in the first region is orthogonally aligned to the direction of ion motion in the second region.

5. The apparatus of claim 1, wherein the direction of ion motion in the first region is aligned in the same direction to the direction of ion motion in the second region.

6. The apparatus of claim 1, wherein the first region and the second region are aligned at any angle between 0°-359° relative to one another.

7. A method of ion peak compression, comprising:
introducing ions into a device having a first region and a second region separate from the first region;
applying a first electric field to the first region for dispersing the ions into a plurality of ion packets based on mobility of the ions; and applying a second electric field to the second region to form an intermittent traveling wave having a duty cycle, and configured to merge two or more adjacent ion packets of the plurality of ion packets by varying the duty cycle.

8. The method of claim 7, further comprising varying the duty cycle of the intermittent traveling wave to control the regrouping or merging of the ion packets.

9. The method of claim 7, wherein the first electric field is a traveling wave.

10. The method of claim 7, wherein the direction of ion motion in the first region is orthogonally aligned to the direction of ion motion in the second region.

11. The method of claim 7, wherein the direction of ion motion in the first region is aligned in the same direction as the direction of ion motion in the second region.

12. The method of claim 7, wherein the first region and the second region are aligned at any angle between 0°-359° relative to one another.

13. The method of claim 7, wherein the intermittent traveling wave merges ions from two or more trapping regions into one.

14. The method of claim 7, wherein the intermittent traveling wave merges ions from four or more trapping regions into one.

15. The method of claim 7, wherein the intermittent traveling wave is replaced with a non-intermittent traveling wave after a predetermined range of ion packets are regrouped or merged prior to detection.

16. A method of ion peak compression comprising:
introducing ions into a device having a first region and a second region separate from the first region;
applying a first electric field to the first region for dispersing the ions into a plurality of ion packets based on mobility of the ions; and
applying a second electric field to the second region to form an intermittent traveling wave having a duty cycle, and configured to merge two or more adjacent ion packets of the plurality of ion packets by varying the duty cycle;
wherein the merged ion packet is temporally narrower than the two or more adjacent ion packets.

17. The method of claim 16, further comprising varying the duty cycle of the intermittent traveling wave to control the regrouping or merging of the ion packets.

18. The method of claim 16, wherein the first electric field is a traveling wave field.

19. The method of claim 16, wherein the first region and the second region are aligned at any angle between 0°-359° relative to one another.

20. The method of claim 16, wherein the intermittent traveling wave merges ions from two or more trapping regions into one.

21. The method of claim 16, wherein the intermittent traveling wave merges ions from four or more trapping regions into one.

22. The method of claim 16, wherein the intermittent traveling wave is replaced with a non-intermittent traveling wave after a predetermined range of ion packets are regrouped or merged and prior to detection.

23. A method of increasing resolution of ions in ion mobility spectrometry (IMS) comprising:
introducing ions into an IMS device having a first region, a second region, and a third region, wherein the first, second and third regions do not overlap;
separating the ions into a plurality of ion packets according to their mobilities by applying a traveling wave (TW) to the first region;
merging two or more adjacent ion packets of the plurality of ion packets by applying a second intermittent traveling wave having a duty cycle to the second region and varying the duty cycle therein; and
reversing the TW so that no separation occurs as the ion packets are moved back to a position prior to the separating step.

24. The method of claim 23, further comprising, after the step of reversing the TW, compressing the ion packets by applying a third intermittent traveling wave including a varying duty cycle therein to the third region.

25. The method of claim 23, wherein no ion separation occurs during the reversing step.

26. The method of claim 23, wherein the reversing step further comprises decreasing the speed or increasing the amplitude of the TW.

27. The method of claim 23, wherein the method effectively increases a path length for IMS separations without physically increasing the IMS device.

28. An apparatus for increasing resolution of ions in ion mobility spectrometry (IMS) comprising:
a separation region configured to receive ions and generates a constant or variable electric field traveling in a first direction for separating the ions into a plurality of ion packets according to mobility of the ions;
an ion compression region separate from the separation region for merging two or more adjacent ion packets to generate a merged ion packet, the ion compression region configured to generate a second electric field having a duty cycle travelling in a second direction, wherein the second electric field generates the merged ion packet by varying the duty cycle, and drives the merged ion packet in the second direction, and
wherein the second direction is reverse of the first direction.

29. The apparatus of claim 28, wherein the IMS device is a SLIM IMS device.

30. An apparatus for increasing resolution of ions in ion mobility spectrometry (IMS) comprising:
an IMS device configured to receive ions, and to generate a constant or variable electric field for partially separating the received ions into a plurality of ion packets according to their mobilities;
a first ion compressor configured to receive the plurality of ion packets and to generate an electric field having a duty cycle therein for merging two or more adjacent ion packets of the plurality of ion packets by varying the duty cycle after separation by the IMS device; and
a second ion compressor separate from the first ion compressor and configured to receive the plurality of ion packets after passage through the ion separator and the first ion compressor and to compress one or more ion packets of the plurality of ion packets so as to produce a final separation with much greater peak intensities and S/N.

31. The apparatus of claim 30 wherein the IMS device is a SLIM IMS device.

* * * * *